United States Patent [19]

Lattrell et al.

[11] 4,118,509
[45] Oct. 3, 1978

[54] 3,5,5-TRIMETHYLHEXANOYL FERROCENE

[75] Inventors: Rudolf Lattrell; Heinrich Kief, both of Konigstein; Hermann Bähr, Kelkheim, all of Fed. Rep. of Germany

[73] Assignee: Hoechst Aktiengesellschaft, Frankfurt am Main, Fed. Rep. of Germany

[21] Appl. No.: 799,973

[22] Filed: May 24, 1977

[30] Foreign Application Priority Data

May 26, 1976 [DE] Fed. Rep. of Germany ....... 2623486

[51] Int. Cl.$^2$ .............................................. C07F 15/02
[52] U.S. Cl. ............................... 424/295; 260/439 CY
[58] Field of Search .................. 260/439 CY; 424/295

[56] References Cited

U.S. PATENT DOCUMENTS

| 3,432,533 | 3/1969 | Rosenberg | 260/439 CY |
| 3,960,911 | 6/1976 | Suschitzky et al. | 260/439 CY |
| 3,966,783 | 6/1976 | Suschitzky et al. | 260/439 CY |
| 4,036,983 | 7/1977 | Rutherford et al. | 260/439 CY |

FOREIGN PATENT DOCUMENTS

| 869,504 | 5/1961 | United Kingdom | 260/439 CY |
| 819,108 | 8/1959 | United Kingdom | 260/439 CY |
| 864,197 | 3/1961 | United Kingdom | 260/439 CY |
| 898,633 | 6/1962 | United Kingdom | 260/439 CY |

OTHER PUBLICATIONS

Rosenblum, Chemistry of the Iron Group Metallocenes, John Wiley & Sons, N.Y., Pt I, pp. 91–93, (1965).

*Primary Examiner*—Helen M. S. Sneed
*Attorney, Agent, or Firm*—Curtis, Morris & Safford

[57] ABSTRACT

3,5,5-Trimethylhexanoyl ferrocene of the formula

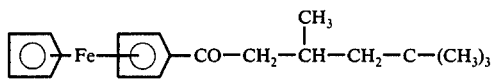

a process for its manufacture, medicaments containing this compound and the use thereof for the treatment of sideropeniasymptoms and sideropenic anaemiae.

3 Claims, No Drawings

3,5,5-TRIMETHYLHEXANOYL FERROCENE

The invention relates to 3,5,5-trimethylhexanoylferrocene of the formula

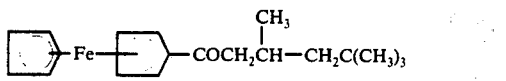

which is distinguished by its extraordinary activity in the treatment of sideropenia symptoms and sideropenic anaemiae.

The invention also relates to a process for the manufacture of ferrocene derivatives of the formula I, pharmaceutical preparations that contain these or comprise these, and to the use thereof in a, or as a, medicament.

The process for the manufacture of 3,5,5-trimethylhexanoyl ferrocene is characterized in that ferrocene is reacted in an inert solvent, in the presence of a Friedel Crafts catalyst, with 3,5,5-trimethylhexanoyl halide or 3,5,5-trimethylhexanoic acid anhydride.

Processes for the manufacture of acylated ferrocene are known (British Pat. Nos. 869 504, 819,108). According to these, ferrocene is reacted with the appropriate acid chloride or acid anhydride under Friedel Crafts conditions, that is, in the presence of Lewis acids, such as, aluminium trichloride, borotrifluoride, zinc chloride, hydrogen fluoride or polyphosphoric acid, in solvents that are inert under the conditions of the reaction, such as, for example, carbon disulfide, ethers, nitromethane or ethylene chloride.

When using aluminium chloride, diacyl compounds are preferentially obtained, whereas in the presence of hydrogen fluoride or polyphosphoric acid monoacyl compounds are produced.

The process according to the invention is preferably carried out with isononanoic acid chloride in the presence of aluminium chloride and methylene chloride as solvent.

In the preparation of the compound I according to the invention, it was surprising that this can be obtained in a good yield in the form of a monoacyl ferrocene compound when using aluminium chloride under the test reaction conditions used. In comparison with, for example, hydrogen fluoride, the use of aluminium chloride has the advantage that it is not dangerous to handle and is simpler to meter in.

In accordance with the process of the invention, ferrocene is reacted with 3,5,5-trimethylhexanoyl halide or 3,5,5-trimethylhexanoic acid anhydride, which is used in an at least equimolar quantity or up to a 10% excess, in an inert solvent such as, methylene dichloride, ethylene dichloride, carbon disulfide, and preferably in the presence of aluminium trichloride, the quantity of which, expressed in moles corresponds to the quantity of isononanoic acid halide or isononanoic acid anhydride used.

The reaction is carried out between $-30°$ and $80°$ C., preferably between $-10°$ and $30°$ C.

In a preferred method for carrying out the process, either the acid chloride can be added dropwise to the ferrocene and aluminium chloride in methylene chloride, or it is possible to add to the suspension of aluminium chloride in methylene chloride, a mixture of ferrocene and acid chloride, dissolved in methylene chloride. A particularly pure product is obtained in a good yield if a mixture of acid chloride and aluminium chloride in methylene chloride is added to the solution of ferrocene in methylene chloride, or if aluminium chloride is added in portions to a solution of ferrocene and isononanoic acid chloride in methylene chloride.

The compound according to the invention is extremely effective in the treatment of sideropenia symptoms and sideropenic anaemiae (anaemiae caused by repeated bloodletting). Thus, the results of an iron-deficient diet for young male rats, such as retarded development of body weight, marked decrease of hemoglobin, of the hematocrit and of the serum iron as well as a slight drop in the number of erythrocytes, is fully compensated by administering this compound with an iron content of 1.6 mg/animal on the first and third day and 5.2 mg of iron/animal on the 27th and 29th test day until the end of the test on the 46th day. The effects of this test on young mice fed on an iron-deficient diet with an average starting weight of 11.8 g were the same. Anaemia in rats produced by bloodletting six times within 12 days can be compensated by 3 administrations of 150 mg of the compound/kg of body weight over a period of 14 days with a simultaneous iron-free diet. At the end of the test, these rats, in comparison with rats of the same weight fed on a normal diet, have increased liver ferritin values and a higher iron content in the liver ferritin.

The compound is resorbed well by peroral administration. The excretion of unchanged substance in the urine of the rat after a single administration of 300 mg/kg is below one part per thousand. The substance is furthermore distinguished by a very low toxicity. The average lethal dose is in the case of rats 8,260 mg/kg and in the case of mice 2,950 mg/kg (administered in glycerine fatty acid esters, for example Miglyol ® 812).

The compound is metabolised in the liver, that is, the iron is released from the compound and incorporated in ferritin, and in the case of repeated administration it is incorporated in ferritin and lysosomally in hemosiderin. In normal animals, repeated administration of the compound results in overloading the organism with iron. Administration once or twice induces an increased apoferritin synthesis of the liver cells and brings about a higher iron content in the liver ferritin. This mechanism, which can be detected by biochemical determination of the ferritin protein and of its iron content, was quantitatively determined in rats, guinea pigs and Beagle hounds and confirmed by histological comparison tests. In the tests, the increase and the higher iron content in the ferritin is recognisable in a Berlin-blue reaction in the form of a uniform blue shading of the cytoplasm of the liver cells, and any hemosiderin that may have formed is recognisable in the form of fine blue grains.

The compound according to the invention is clearly superior to known ferrocene derivatives in its capability to increase the iron of the liver that can be used to form blood. This is shown by comparison tests with the ferrocene derivatives 2a–d described in British Pat. Nos. 819 108 and 869 504, wherein 2d is, according to details in the literature (Brit. J. Pharmacol. 24, 352, 1965) the best, especially regarding its ability to utilize the iron.

2a. hexahydrobenzoyl-ferrocene
2b. 1,1'-di-(3,5,5-trimethyl-hexanoyl)-ferrocene
2c. 1,1'-di-hexahydrobenzoyl-ferrocene
2d. 1,1'-di-neopentyl ferrocene The compounds were administered to 6 male rats and 6 male mice on two successive days in individual doses corresponding to an iron content of 52.2 mg Fe per kg of animal. 24 hours after the 2nd administration the animals were killed.

Histologically, the compound according to the invention in comparison with 2a and 2b exhibits a substantially greater increase of the liver ferritin, and individual hemosiderin particles are observed. The compounds 2c and 2d do not cause any histologically recognisable increase of the liver ferritin. The quantitative determination of the liver ferritin protein and its iron content (table) confirm these findings. For this, ferritin is isolated from the liver by thermal denaturation, ammonium sulfate fractionation and gel filtration, and the protein is determined by amino acid analysis and the iron content by atom absorption. It is evident from the values in the table that the ferritin protein and the iron saturation of the ferritin have increased more markedly after administration of the compound I according to the invention as compared with the known compounds 2a–d.

Table

Analysis of the ferritin from rat livers 1)

| Substance | Ferritin-iron μg/g tissue | Ferritin-protein μg/g tissue | Ratio of iron to protein | Dosage 2) mg/kg |
|---|---|---|---|---|
| 1 | 652 | 761 | 0.85 | 2 × 300 |
| 2 a | 209 | 479 | 0.43 | 2 × 277 |
| 2 b | 148 | 567 | 0.26 | 2 × 436 |
| 2 c | 94 | 224 | 0.42 | 2 × 380 |
| 2 d | 61 | 130 | 0.38 | 2 × 305 |
| Control | 59 | 365 | 0.16 | — |

1) Average values from 6 animals
2) Corresponds to 52.2 mg Fe/kg of animal

The compound according to the invention is used as active component in pharmaceutical preparations, preparations for oral administration being preferred. The preparations may contain the active substance per se or in admixture with other substances. The level of the dose administered obviously depends on the type of treatment desired and on the method of administration. In the case of oral administration satisfactory results are obtained with doses of 10 to 300 mg of active substance per kg of animal body weight; in the case of man the daily dosage varies between 50 and 1000 mg of active substance per person, wherein individual doses of 50 to 1000 mg, in particular 50 to 250 mg, may be administered preferably once to three times daily.

The forms of preparation to be considered for oral administration are, for example, tablets, push-fit capsules, alcoholic or oily suspensions or solutions. Suitable inert carriers for tablets and dragees are, for example, magnesium carbonate, lactose, stearic acid, milk sugar or maize starch, with the addition of other substances such as, for example, magnesium stearate. The compositions may be obtained by dry or moist granulation. The oily carrier substances or solvents considered are especially vegetable, animal or synthetic oils, such as cod liver oil or sunflower oil.

The active compound can also be made up into a paste, chewing gum, tablets that are to be chewed, or a drink ampoule or may be combined with foodstuffs. The preparations may also contain other pharmacologically active components, such as vitamins, for example, vitamin $B_{12}$, vitamin C or folic acid, analgesic agents, such as aspirin, or anthelmintic agents. The preparations may further contain, as additions, preservatives and stabilizers, sweeteners or flavoring substances. A suitable form of preparation for oral administration is, for example, gelatin capsules that contain a solution of 150 mg glycerine fatty acid ester, for example Miglyol ®.

The invention is explained by the following Examples.

EXAMPLE 1

29.3 g (0.22 mole) $AlCl_3$ are added in portions in a uniform manner, over a period of 120 minutes, to a solution cooled to 5° C. of 37.2 g (0.2 mole) of ferrocene and 39 g (0.22 mole) of 3,5,5-trimethylhexanoyl chloride in 600 ml of methylene chloride.

Stirring is carried out for 1¾ hours at 10° to 15° C., the violet-colored solution is poured into 1.5 l of ice water and shaken, and the organic phase is separated and washed successively with water and saturated aqueous sodium bicarbonate solution and then twice again with water. The oily residue of the organic phase is dissolved in 100 ml of methanol. By adding 100 ml of water, an oil is precipitated which is crystallised by triturating. The crude crystal sludge is suction filtered, washed with water, cooled and washed once with 100 ml, then with 50 ml of methanol at −60° C. The remaining red-colored product melts at 43°–45° C. after drying. Further 3,5,5-trimethylhexanoylferrocene is isolated from the oily residue of the methanolic washing liquor.

EXAMPLE 2

A mixture of 29.3 g $AlCl_3$ and 39 g of 3,5,5-trimethylhexanoyl chloride in 200 ml of methylene chloride is added dropwise at 15° C., over a period of 1 hour, to 37.2 g of ferrocene in 400 ml of methylene chloride. After standing for 4 hours at 25° C., extraction is carried out with 1 l of ice water, the organic phase is separated and washed with water, $NaHCO_3$ solution and again with water. The compound is isolated as in Example 1. The red-colored product has a melting point of 44°–45° C.

We claim:
1. 3,5,5-Trimethylhexanoyl-ferrocene of the formula

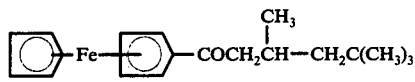

2. A medicament for the treatment of sideropenia symptoms and sideropenic anemia, said medicament consisting essentially of an effective amount of 3,5,5-trimethylhexanoyl-ferrocene and a pharmacologically acceptable carrier.

3. A method for the treatment of sideropenia symptoms and sideropenic anaemiae in a patient requiring said treatment which comprises administering to said patient an effective amount of 3,5,5-trimethylhexanoyl-ferrocene.

* * * * *